US012605366B2

(12) United States Patent
Traas et al.

(10) Patent No.: US 12,605,366 B2
(45) Date of Patent: Apr. 21, 2026

(54) TELMISARTAN FOR THE TREATMENT OF HYPERTENSION IN DOGS

(71) Applicants: BOEHRINGER INGELHEIM VETMEDICA GMBH, Ingelheim am Rhein (DE); University of Georgia Research Foundation, Inc., Athens, GA (US)

(72) Inventors: Anne Michelle Traas, Saint Joseph, MO (US); Amanda Erickson Coleman, Bogart, GA (US); Bianca Natália Ferreira De Moura Lourenco, Athens, GA (US); Kate Elizabeth Creevy, College Station, TX (US); Scott Alan Brown, Winterville, GA (US)

( * ) Notice: Subject to any disclaimer, the term of this patent is extended or adjusted under 35 U.S.C. 154(b) by 765 days.

(21) Appl. No.: 17/596,356

(22) PCT Filed: Apr. 30, 2020

(86) PCT No.: PCT/US2020/030581

§ 371 (c)(1),
(2) Date: Dec. 8, 2021

(87) PCT Pub. No.: WO2021/006942

PCT Pub. Date: Jan. 14, 2021

(65) Prior Publication Data

US 2022/0226290 A1      Jul. 21, 2022

Related U.S. Application Data

(60) Provisional application No. 62/871,749, filed on Jul. 9, 2019.

(51) Int. Cl.
| | |
|---|---|
| *A61K 31/4184* | (2006.01) |
| *A61K 45/06* | (2006.01) |
| *A61P 9/12* | (2006.01) |

(52) U.S. Cl.
CPC .......... *A61K 31/4184* (2013.01); *A61K 45/06* (2013.01); *A61P 9/12* (2018.01)

(58) Field of Classification Search
CPC ...... A61K 31/401; A61K 31/4184; A61P 9/12
See application file for complete search history.

(56) References Cited

U.S. PATENT DOCUMENTS

| | | | |
|---|---|---|---|
| 4,355,040 | A | 10/1982 | Furukawa et al. |
| 4,448,778 | A | 5/1984 | Lynch |
| 4,880,804 | A | 11/1989 | Carini et al. |
| 5,237,997 | A | 8/1993 | Greubel et al. |
| 5,331,162 | A | 7/1994 | Silver et al. |
| 5,591,762 | A | 1/1997 | Hauel et al. |
| 5,846,962 | A | 12/1998 | Suzuki et al. |
| 5,965,592 | A | 10/1999 | Buhlmayer et al. |
| 6,028,091 | A | 2/2000 | Hill |
| 6,204,281 | B1 | 3/2001 | Webb et al. |
| 6,331,162 | B1 | 12/2001 | Mitchell |
| 6,358,986 | B1 | 3/2002 | Schneider |
| 6,410,742 | B1 | 6/2002 | Schneider |
| 6,589,547 | B1 | 7/2003 | Igari et al. |
| 6,737,432 | B2 | 5/2004 | Donsbach et al. |
| 7,208,508 | B2 | 4/2007 | Daemmgen et al. |
| 8,005,624 | B1 | 8/2011 | Starr |
| 8,772,278 | B2 | 7/2014 | Stark et al. |
| 8,838,209 | B2 | 9/2014 | Mestha et al. |
| 8,870,782 | B2 | 10/2014 | Futatsuyama et al. |
| 8,871,795 | B2 | 10/2014 | Mohr et al. |
| 9,011,346 | B2 | 4/2015 | Wiard et al. |
| 9,241,637 | B2 | 1/2016 | Wiard et al. |
| 9,308,197 | B2 | 4/2016 | Stark et al. |
| 9,585,873 | B2 | 3/2017 | Stark et al. |
| 9,833,151 | B2 | 12/2017 | Wiard et al. |
| 9,949,954 | B2 | 4/2018 | Stark et al. |
| 9,949,964 | B2 | 4/2018 | Racheboeuf |
| 10,314,782 | B2 | 6/2019 | Mohr et al. |
| 10,349,847 | B2 | 7/2019 | Kwon et al. |
| 10,357,479 | B2 | 7/2019 | Stark et al. |
| 10,537,523 | B2 | 1/2020 | Mohr et al. |
| 10,905,676 | B2 | 2/2021 | Anke et al. |
| 2002/0037095 | A1 | 3/2002 | Cheng |
| 2002/0094997 | A1 | 7/2002 | Schneider et al. |
| 2003/0144583 | A1 | 7/2003 | Cheng et al. |
| 2004/0033258 | A1 | 2/2004 | Koike |

(Continued)

FOREIGN PATENT DOCUMENTS

| | | |
|---|---|---|
| CA | 2352436 A1 | 7/2000 |
| CA | 2463146 A1 | 5/2003 |

(Continued)

OTHER PUBLICATIONS

Gonzalez, S.G. et al., "Telmisartan versus benazepril on the management of systemic hypertension in dogs with hyperadrenocorticism" Journal of Veterinary Internal Medicine, Apr. 2019, vol. 33, No. 2, p. 1083, Abstract No. ESVE-P-15.

Yusuke Sakai, et al., Antiproteinuric effect of telmisartan in dogs with protein-leaking nephropathy, Japanese Association of Veterinary Nephrology and Urology) 2018, vol. 10, No. 1, pp. 44-49.

Harkevič D.A., Farmakologiâ [Pharmacology], Moscow, 2006, p. 62.

Written Opinion of the International Search Authority WO2021006941, Jan. 14, 2021.

Written Opinion of the International Search Authority WO2021006942, Jan. 14, 2021.

Acierno et al., ACVIM consensus statement: Guidelines for the identification, evaluation, and management of systemic hypertension in dogs and cats. J Vet Intern Med. 2018, 32, 1803-1822.

(Continued)

*Primary Examiner* — Sarah Pihonak

(74) *Attorney, Agent, or Firm* — Katrina Bergbauer

(57)      ABSTRACT

The present invention relates to telmisartan or a pharmaceutically acceptable salt thereof as a medicament for the treatment of hypertension in dogs, wherein the therapeutically effective amount of telmisartan is administered in a daily dosage amount that is varied over a treatment period.

15 Claims, 2 Drawing Sheets

(56) References Cited

U.S. PATENT DOCUMENTS

| | | |
|---|---|---|
| 2004/0110813 A1 | 6/2004 | Nakatani et al. |
| 2004/0219208 A1 | 11/2004 | Kawamura et al. |
| 2005/0070594 A1 | 3/2005 | Kauschke et al. |
| 2005/0186274 A1 | 8/2005 | Kohlrausch |
| 2005/0272649 A1 | 12/2005 | Hruska et al. |
| 2007/0026026 A1 | 2/2007 | Delmarre et al. |
| 2007/0155679 A1 | 7/2007 | Daemmgen et al. |
| 2008/0146543 A1 | 6/2008 | Stark et al. |
| 2008/0183232 A1 | 7/2008 | Voss et al. |
| 2010/0100160 A1 | 4/2010 | Edman et al. |
| 2010/0292578 A1 | 11/2010 | Sato |
| 2011/0260176 A1 | 10/2011 | Onoe et al. |
| 2012/0078123 A1 | 3/2012 | Futatsuyama et al. |
| 2012/0095069 A1 | 4/2012 | Mohr et al. |
| 2012/0245439 A1 | 9/2012 | Andre et al. |
| 2013/0030259 A1 | 1/2013 | Thomsen et al. |
| 2013/0190373 A1 | 7/2013 | Stark et al. |
| 2013/0310700 A1 | 11/2013 | Wiard et al. |
| 2014/0288138 A1 | 9/2014 | Stark et al. |
| 2014/0364473 A1 | 12/2014 | Mohr et al. |
| 2015/0282718 A1 | 10/2015 | Wiard et al. |
| 2016/0045117 A1 | 2/2016 | Liu et al. |
| 2016/0095522 A1 | 4/2016 | Wiard et al. |
| 2016/0256108 A1 | 9/2016 | Yun et al. |
| 2016/0361300 A1 | 12/2016 | Schwartz et al. |
| 2016/0374619 A1 | 12/2016 | Borkholder et al. |
| 2017/0000350 A1 | 1/2017 | Kwon et al. |
| 2017/0127959 A1 | 5/2017 | Paulussen et al. |
| 2017/0128423 A1 | 5/2017 | Stark et al. |
| 2017/0188963 A1 | 7/2017 | Banet et al. |
| 2017/0238818 A1 | 8/2017 | Gaurav et al. |
| 2017/0245767 A1 | 8/2017 | Ferber et al. |
| 2017/0360316 A1 | 12/2017 | Gu et al. |
| 2018/0125376 A1 | 5/2018 | Denney, Jr. et al. |
| 2018/0132736 A1 | 5/2018 | Silverman |
| 2018/0193317 A1 | 7/2018 | Stark et al. |
| 2018/0199824 A1 | 7/2018 | Centen et al. |
| 2018/0303428 A1 | 10/2018 | Yamashita et al. |
| 2018/0360323 A1 | 12/2018 | Lui |
| 2019/0008431 A1 | 1/2019 | Bechtel et al. |
| 2019/0008831 A1 | 1/2019 | Albrecht et al. |
| 2019/0099116 A1 | 4/2019 | Wiese et al. |
| 2020/0205681 A1 | 7/2020 | Putila et al. |
| 2020/0305740 A1 | 10/2020 | Quan et al. |
| 2021/0106564 A1 | 4/2021 | Albrecht et al. |
| 2021/0113094 A1 | 4/2021 | Anliker et al. |
| 2021/0113155 A1 | 4/2021 | Anliker et al. |
| 2021/0244302 A1 | 8/2021 | Lizio et al. |
| 2022/0218671 A1 | 7/2022 | Traas et al. |
| 2025/0195525 A1 | 6/2025 | Haag-Diergarten et al. |

FOREIGN PATENT DOCUMENTS

| | | | |
|---|---|---|---|
| CN | 1422153 A | 6/2003 | |
| CN | 1765362 A | 5/2006 | |
| CN | 1849998 A | 10/2006 | |
| CN | 101522191 A | 9/2009 | |
| CN | 102300538 A | 12/2011 | |
| CN | 102458363 A | 5/2012 | |
| CN | 108801421 A | 11/2018 | |
| CN | 110251105 A | 9/2019 | |
| DE | 1023027 B | 1/1958 | |
| DE | 10335027 A1 | 2/2005 | |
| EP | 0253310 B1 | 1/1988 | |
| EP | 0323841 B1 | 7/1989 | |
| EP | 0324377 B1 | 7/1989 | |
| EP | 0420237 B1 | 4/1991 | |
| EP | 0443983 B1 | 8/1991 | |
| EP | 0459136 B1 | 12/1991 | |
| EP | 0475206 A2 | 3/1992 | |
| EP | 0502314 B1 | 9/1992 | |
| EP | 0504888 A1 | 9/1992 | |
| EP | 0514198 A1 | 11/1992 | |
| EP | 1579862 A1 | 9/2005 | |
| EP | 1908469 A1 * | 4/2008 | ............ A61K 31/00 |

| | | | |
|---|---|---|---|
| EP | 2420232 A2 | 2/2012 | |
| JP | H11315034 A | 11/1999 | |
| JP | 2002172094 A | 6/2002 | |
| JP | 2006502194 A | 1/2006 | |
| JP | 2008104667 A | 5/2008 | |
| JP | 2008518888 A | 6/2008 | |
| JP | 2008237686 A | 10/2008 | |
| JP | 2013169464 A | 9/2013 | |
| JP | 2017000415 A | 1/2017 | |
| RU | 2008135692 A | 3/2010 | |
| WO | 1985003211 A1 | 8/1985 | |
| WO | 1991014679 A1 | 10/1991 | |
| WO | 1992010182 A1 | 6/1992 | |
| WO | 1993020816 A1 | 10/1993 | |
| WO | 1995026188 A1 | 10/1995 | |
| WO | 1996031234 A1 | 10/1996 | |
| WO | 1997049392 A1 | 12/1997 | |
| WO | 1999044590 A1 | 9/1999 | |
| WO | 2000043370 A1 | 7/2000 | |
| WO | 2001078699 A2 | 10/2001 | |
| WO | 2002092081 A1 | 11/2002 | |
| WO | 2003004068 A1 | 1/2003 | |
| WO | 2003037876 A1 | 5/2003 | |
| WO | 2004014308 A2 | 2/2004 | |
| WO | 2004028505 A1 | 4/2004 | |
| WO | 2005070463 A2 | 8/2005 | |
| WO | 2005123070 A1 | 12/2005 | |
| WO | 2006048208 A1 | 5/2006 | |
| WO | 2007092469 A2 | 8/2007 | |
| WO | 2008040774 A2 | 4/2008 | |
| WO | 2008110599 A1 | 9/2008 | |
| WO | 2010063114 A1 | 6/2010 | |
| WO | 2010133638 A1 | 11/2010 | |
| WO | 2015127193 A1 | 8/2015 | |
| WO | 2017171228 A1 | 10/2017 | |
| WO | 2019008077 A1 | 1/2019 | |
| WO | 2019170903 A1 | 9/2019 | |
| WO | 2021006941 A1 | 1/2021 | |
| WO | 2021006942 A1 | 1/2021 | |
| WO | 2021074292 A1 | 4/2021 | |
| WO | 2021074297 A1 | 4/2021 | |
| WO | 2024240632 A1 | 11/2024 | |
| WO | 2024240633 A1 | 11/2024 | |
| WO | 2025125409 A1 | 6/2025 | |

OTHER PUBLICATIONS

Ames et al. Effects of high doses of enalapril and benazepril on the pharmacologically activated renin-angiotensin-aldosterone system in clinically normal dogs. Am J Vet Res 2015; 76:1041-50.

Brown et al., Evaluation of the effects of inhibition of angiotensin converting enzyme with enalapril in dogs with induced chronic renal insufficiency. Am J Vet Res 2003; 64, 321-327.

Brown et al. Guidelines for the identification, evaluation, and management of systemic hypertension in dogs and cats. J Vet Intern Med 2007; 21:542-58.

Brown et al. IRIS Canine GN Study Group Standard Therapy Subgroup, Consensus Recommendations for Standard Therapy of Glomerular Disease in Dogs. J Vet Intern Med 2013; 27:S27-43.

Bugbee et al., Telmisartan Treatment of Refractory Proteinuria in a Dog. Journal of Veterinary Internal Medicine, 2014, vol. 28, No. 6, 1871-1874.

Caro-Vadillo et al., Effect of a combination of telmisartan and amlodipine in hypertensive dogs. Veterinary Record Case Reports 2018, vol. 6 No. 2, p. e000471.

European Medicines Agency. PRAC recommends against combined use of medicines affecting the renin-angiotensin (RAS) system, 2014. EMA EMA/196502/2014.

Geigy et al. Occurrence of systemic hypertension in dogs with acute kidney injury and treatment with amlodipine besylate. J Small Anim Pract 2011; 52:340-6.

Grauer et al., Effects of enalapril versus placebo as a treatment for canine idiopathic glomerulonephritis. J Vet Intern Med 2000, 14, 526-533.

Grodecki et al., Treatment of X-linked hereditary nephritis in Samoyed dogs with angiotensin converting enzyme (ACE) inhibitor. J Comp Pathol 1997, 117, 209-225.

(56)            References Cited

OTHER PUBLICATIONS

Konta et al.,Evaluation of the inhibitory effects of telmisartan on drug-induced renin-angiotension-aldosterone system activation in normal dogs. Journal of Veterinary Cardiology 2018, vol. 20 No. 5, p. 376-383.

Kwon et al.,Successful management of proteinuria and systemic hypertension in a dog with renal cell carcinoma with surgery, telmisartan, and amlodipine. Can Vet J 2018, 59(7), 759-762.

Lorenço, Efficacy of Telmisartan for the Treatment of Persistent Canine Renal Proteinuria. AVCIM Forum 2019. Published May 21, 2019 at https://www.eventscribe.com/2019/ACVIM/agenda.asp?pfp=agenda.

Schierok et al., Effects of telmisartan on Renal Excretory Function in Conscious Dogs. Journal of International Medical Research 2001, 131-139.

Schmieder et al. A guide for easy- and difficult-to-treat hypertension. Int J Cardiol 2014; 172:17-22.

Tjostheim et al. Effects of Toceranib Phosphate on Systolic Blood Pressure and Proteinuria in Dogs. J Vet Intern Med 2016; 30:951-7.

Wienen et al. A Review on Telmisartan: A Novel, Long-Acting Angiotensin II-Receptor Antagonist. Cardiovasc Drug Rev 2000;18:127-54.

Martin, José FV, Luciana NC Martin, and José P. Cipullo. "Pharmacologic treatment for prehypertension: to treat or not to treat?" Recent Patents on Cardiovascular Drug Discovery (Discontinued) 4.2 (2009): 133-141.

Maruo et al., "Polymorphism of UDP-Glucuronosyltransferase and Drug Metabolism." Current Drug Metabolism, vol. 6, 2005, pp. 91-99.

Mathur et al., "Evaluation of a technique of inducing hypertensive renal insufficiency in cats". American Journal of Veterinary Research, vol. 65, No. 7, Jul. 2004, pp. 1006-1013.

Mishina et al., "Non-invasive Blood Pressure Measurements in Cats: Clinical Significance of Hypertension Associated with Chronic Renal Failure." The Journal of Veterinary Medical Science, vol. 60, No. 7, 1998, pp. 805-808.

Norikazu et al., "Comparison of angiotensin II receptor antagonists and angiotensin converting enzyme inhibitors on a dog suffering mild mitral insufficiency". Annual Meeting of the Japanese Society of Veterinary Science, vol. 137, 2004, p. 140.

Ono et al., "Characteristics of the Long-Acting Sartan Telmisartan". Circulation Control, vol. 23, No. 4, 2002, pp. 462-466.

Osweiler, Gary D., "Toxicological Concepts: Factors that Influence Toxicology", General Toxicological Principles, in Small Animal Toxicology, Elsevier, Inc., St. Louis, MO, 2006, p. A17.

Pace, Charlotte. "Canine and feline hypertension." The Veterinary Nurse 14.2 (2023): 75-82.

Perrier et al., "In vitro N-glucuronidation of SB 47436 (BMS 186295), a new AT1 nonpeptide angiotensin II receptor antagonist, by rat, monkey and human hepatic microsomal fractions." Abstract, The Journal of Pharmacology and Experimental Therapeutics, vol. 271, No. 1, Oct. 1994, pp. 91-99 (p. A-10).

Pershadsingh et al., "Insulin-Sensitizing Effects of Telmisartan". Diabetes Care, vol. 27, No. 4, Apr. 2004, p. 1015.

Polzin et al., "Treating Feline Kidney Disease: An Evidence-Baed Approach". North American Veterinary Conference Proceedings, Jan. 7, 2006, pp. 1-6. [Accessed at http://www.iknowledgenow.com/article.cfm?documentID=2817transactionKey . . . on Dec. 16, 2014].

Resampling (statistics)(retrieved from internet on Apr. 7, 2025) Retrieved from ,https://en.wikpedia.org/w/index.php?title=Resampling_(statistics) & oldid=917587664. Sep. 24, 2019.

Rodriguez-Iturbe et al., "Early treatment with cGMP phosphodiesterase inhibitor ameliorates progression of renal damage". Kidney International, vol. 68, 2005, pp. 2131-2142.

Schiweck et al., "Sugar Alcohols". Ullmann's Encyclopedia of Industrial Chemistry, Wiley-VCH Verlag GmbH & Co. KGaA, Weinheim, 2012, pp. 1-37.

Semintra—Prescription Animal Remedy, Jun. 6, 2016, Retrieved From the Internet: http://files.boehringer.com.au/files/CMI/Semintra%20ANZ.pdf [retrieved on Oct. 12, 2018].

Sharpe, Miriam, Blair Jarvis, and Karen L. Goa. "Telmisartan: a review of its use in hypertension." Drugs 61.10 (2001): 1501-1529.

Snively et al., "Chronic Kidney Disease: Prevention and Treatment of Common Complications". American Family Physicians, vol. 70, No. 10, Nov 2004m pp. 1921-1928.

Stebbins et al., "Spinal angiotensin II influences reflex cardiovascular responses to muscle contraction". American Journal of Physiology, vol. 269, No. 4, Part 2, 1995pp. R864-R868.

Suga et al., "Angiotensin II type 1 receptor blockade ameliorates tubulointerstitial injury induced by chronic potassium deficiency". 2002, Kidney International, vol. 61, pp. 951-958.

Summary of Product Information—Semintra, European Medicine Agency, Feb. 28, 2013, pp. 1-32, retrieved from the Internet: URL:https://www.ema.europa.eu/documents/product-information/semintra-epar-product-information_en.pdf [retrieved on Oct. 12, 2018].

Suzuki, Hiromichi, "Investigation of Clinical Benefits of Different Types of ARBs in Treatment of Hypertension Associated with Renal Disease." Progress in Medicine, vol. 26, No. 7, Jul. 2006, pp. 145-151 (1669-1674).

Syme et al., "Survival of Cats with Naturally Occurring Chronic Renal Failure Is Related to Severity of Proteinuria". Journal of Veterinary Internal Medicine, vol. 20, No. 3, 2006, pp. 528-535.

Tran et al., "Modulation of microenvironmental pH and crystallinity of ionizable telmisartan using alkalizers in solid dispersions for controlled release". Journal of Controlled Release, vol. 129, No. 1, 2008, pp. 59-65.

Villar et al., "Ibuprofen, Aspirin and Acetaminophen Toxicosis and Treatment in Dogs and Cats". Veterinary Human Toxicology, vol. 40, No. 3, 1998, pp. 156-162.

Web site: www.merck.com "Chronic Kidney Disease," accessed on Dec. 13, 2010.

Web site: www.merck.com "Tubulointerstitial Nephritis," accessed on Jun. 1, 2009.

White, et al., "Effects of the angiotensin II receptor blockers telmisartan versus valsartan on the circadian variation of blood pressure: impact on the early morning period," Amer Journal of Hypertension, vol. 17, Issue 4, 2004, pp. 347-353.

Written Opinion of the International Search Authority for PCT/EP2007/060531 mailed May 19, 2008.

Written Opinion of the International Search Authority PCT/EP/020079045 (WO2021074297), mailed on Feb. 9, 2021.

Written Opinion of the International Search Authority PCT/EP/2018/068189 (WO2019008077), mailed on Oct. 26, 2018.

Written Opinion of the International Search Authority PCT/EP2020/079040 (WO2021074292A1), mailed on Feb. 9, 2021.

Written Opinion of the International Searching Authority for PCT/EP2010/056895 mailed on Aug. 3, 2010.

Xiao et al., "Regional Hemodynamic Effects of the AT1 Receptor Antagonist CV-11974 in Conscious Renal Hypertensive Rats". Hypertension, vol. 26, 1995, pp. 989-997.

Xue, Jintong. "Chapter 13. Hypertensive Disease". Practical Handbook for the Diagnosis and Treatment of Cardiovascular Disease, First Edition, Zhengzhou University Press, 2005, pp. 480-508.

Yoshida et al., "Metabolic effect of AII receptor antagonists." Ketsuatsu (Blood Pressure), vol. 9, No. 8, 2002, pp. 802-806. (Abstract in English).

Yu, Guoqiang, et al. "Time-dependent blood flow and oxygenation in human skeletal muscles measured with noninvasive near-infrared diffuse optical spectroscopies." Journal of biomedical optics 10.2 (2005): 024027-024027.

Zenchun Li et al. "Progress in Drug Therapy for Dialated Cardiomyopathy" Chinese Medical Abstracts—Geriatrics, 2002, vol. 11, No. 1, pp. 69-72 (Chinese Language).

"Kidney Disease", The Medical Dictionary, pp. 1-5. [Accessed at: http://medical-dictionary.thefreedictionary.com/kidney+disease; accessed Nov. 1, 2015].

Zenchun Li et al. "Progress in Drug Therapy for Dialated Cardiomyopathy" Chinese Medical Abstracts—Geriatrics, 2002, vol. 11, No. 1, pp. 69-72 English translation of introduction paragraph + cited paragraph.

Abstract in English for CN1765362A, 2006.

Abstract in English for JPH11315034A1, 1999.

(56)               References Cited

OTHER PUBLICATIONS

Adamson et al., "The Fate of Sulphadimethoxine in Primates Compared with other Species". Biochemical Journal, vol. 118, 1970, pp. 41-45.

Allen, Andrew L., "The Diagnosis of Acetaminophen toxicosis in cats"., The Canadian Veterinary Journal, vol. 44, No. 6, Jun. 2003, pp. 509-510.

Anonymously, "Bootstrapping (statistics)", https://web.archive.org/web/2019040854026/https://en.wikepedia.or(wiki/Bootstrapping_ (statistics), Wikipedia, XP093129092, Publication date Apr. 8, 2019, 13 pages.

Arenas-Lopez et al., Accuracy of enteral syringes with commonly prescribed paediatric liquid medicines. Archives of Disease in Childhood 2017, 102, 655-659. Published Feb. 24, 2017.

Asiedu-Gyekye et al. "Does losartan prevent cerebral edema? A preliminary study using a vascular compartment model". Medical Science Monitor, vol. 9, No. 3, Mar. 2003, pp. BR127-BR130.

Barnett, Anthony H., et al. "Angiotensin-receptor blockade versus converting-enzyme inhibition in type 2 diabetes and nephropathy." New England Journal of Medicine 351.19 (2004): 1952-1961.

Berny et al., "Animal Poisoning in Europe. Part 2: Companion Animals". The Veterinary Journal, vol. 183, 2010, pp. 255-259.

Bile Excreted Sustained AT1 Receptor Blocker (alternatively 'Biliary excretion type AT1 receptor blocker with prolonged action'), Japanese Pharmacopoeia, Telmisartan tablets, package insert, Nihon Generic Co., Ltd. (Jun. 2017). (English Translation).

Bile Excreted Sustained AT1 Receptor Blocker (alternatively 'Biliary excretion type AT1 receptor blocker with prolonged action'), Japanese Pharmacopoeia, Telmisartan tablets, package insert, Nihon Generic Co., Ltd. (Jun. 2017). (Japanese Language).

Buoncompagni et al., "Treatment of Systemic Hypertension Associated With Kidney Disease." Compendium: Continuing Education for Veterinarians, Vetlearn.com, 2013, pp. E1-E6.

Burnier et al., "Angiotensin Il receptor antagonists". The Lancet, vol. 355, 2000, pp. 637-645.

Caldwell et al., "Drug Metabolism in 'Exotic' Animals". European Journal of Drug Metabolism and Pharmacokinetics, No. 2, 1978, pp. 61-66.

Caldwell et al., "Species Differences in Xenobiotic Conjugation". Xenobiotic Metabolism and Disposition, Proceedings of the 2nd International ISSX Meeting, Kobe, Japan, May 16-20, 1988, pp. 217-224.

Champion et al., "Analysis of the Effects of Candesartan on Responses to Angiotensin II in the Hindquarters Vascular Bed of the Cat". Journal of the American Society of Nephrology, vol. 10, 1999, pp. S101-S103.

Cingolani et al., "The Positive Inotropic Effect of Angiotensin II: Role of Endothelin-1 and Reactive Oxygen Species". Hypertension, vol. 47, No. 4, Apr. 2006, pp. 727-734.

Conlon, Peter D., "Nonsteroidal Drugs Used in the Treatment of Inflammation". Clinical Pharmacology, vol. 18, No. 6, 1988, pp. 1115-1131.

Coronel et al., "Hypertension Treatment in Nondiabetic Advanced Chronic Kidney Disease Patients with Irbesartan. Effect on Serum Uric Acid". Abstract, Journal of Hypertension, vol. 23, Supp. 2, 2005, p. S65.

Court et al., "Molecular Basis for Deficient Acetaminophen Glucuronidation in Cats an Interspecies Comparison of Enzyme Kinetics in Liver Microsomes," 1997, Biochemical Pharmacology, vol. 53, pp. 1041-1047.

Court et al., "Molecular genetic basis for deficient acetaminophen glucuronidation by cats: UGT1A6 is a pseudogene, and evidence for reduced diversity of expressed hepatic UGT1A isoforms". Pharmacogenetics, vol. 10, 2000, pp. 355-369.

Desmet, Lien, and Jeroen van der Meer. "Antihypertensive treatment with telmisartan in a cat with amlodipine-induced gingival hyperplasia." Journal of Feline Medicine and Surgery Open Reports 3.2 (2017): 2055116917745236.

Ebner et al., "Disposition and Chemical Stability of Telmisartan 1-O-acylglucuronide". 1999, The American Society for Pharmacology & Experimental Therapeutics, vol. 27, No. 10, pp. 1143-1149.

Ebner et al., "In vitro flucuronidation of the angiontensin II receptor antagonist telmisartan in the cat: a comparison with other species." Journal of Vetrinary Pharmacology and Therapeutics, vol. 36, 2012, pp. 154-160.

Ettinger et al., "Therapeutic Considerations in Medicine and Disease", Textbook of Veterinary Internal Medicine Diseases of the Dog and Cat, Sixth Edition, vol. 1, Section VI, Table 143, 2005, pp. 530-531.

Garrison et al., "[Pro11, D-Ala12] angiotensin I has rapid onset vasoconstrictor activity in the cat". American Journal of Physiology-Endocrinology and Metabolism, vol. 273, No. 6, 1997, pp. E1059-E1064.

Glaus, A., J. Elliott, and B. Albrecht. "Efficacy of telmisartan in hypertensive cats: results of a large European Clinical Trial 27th ECVIM-CA Congress." Malta: John Wiley & Sons, Ltd (2017). Wiley & Sons, Ltd (2017).

Grauer, Gregory, "ACE Inhibitors and CKD", 2 pages. [Accessed at : http://www.dvm360storage.com/cvc/proceedings/dc/Urology/Grauer/ Grauer,Gregory_ACE_Inhibitors_and_CKD.pdf on Feb. 5, 2015].

Guangxi Agricultural College et al., "Oxidation in acidic solutions". Organic Chemistry, Guangxi People's Publishing House, Dec. 1982, p. 235.

Harley et al., "Proteinuria in dogs and cats." Canadian Veterinary Journal, vol. 53, Jun. 2012, pp. 631-638.

Hiwada, Kunio, "Presentation of New Drug: Telmisartan". Vascular Biology & Medicine, vol. 3, No. 5, 2002, pp. 571-576.

Honjo et al., "Possible Beneficial Effect of Telmisartan on Glycemic Control in Diabetic Subjects". Diabetes Care, vol. 28, No. 2, Fe. 2005, p. 498.

Huskey et al., "N-glucuronidation reactions. I. Tetrazole N-glucuronidation of selected angiotensin II receptor antagonists in hepatic microsomes from rats, dogs, monkeys, and humans." Abstract, Drug Metabolism and Disposition, vol. 21, No. 5, 1993, pp. 792-299 (p. A-9).

Iino et al., "Renoprotective Effect of Losartan in Comparison to Amlodipine in Patients with Chronic Kidney Disease and Hypertension—a Report of the Japanese Losartan Therapy Intended for the Global Reneal Protection in Hypertensive Patients (JLIGHT) Study". Hypertension Research, vol. 27, No. 1, 2004, pp. 21-30.

International Search Report for PCT/EP2007/060531 mailed May 19, 2008.

Israili, Z.H., "Clinical pharmacokinetics of angiotensin II (AT1) receptor blockers in hypertension". Journal of Human Hypertension, vol. 14, Suppl. 1, 2000, pp. S73-S86.

Jensen et al., "Plasma renin activity and angiotensin I and aldosterone concentrations in cats with hypertension associated with chronic renal disease." American Journal of Veterinary Research, vol. 58, No. 5, May 1997, pp. 535-540.

Kemper et al., "Metabolism: A Determinant of Toxicology". Principles and Methods of Toxicology, 5th Edition, Chapter 3, Informa Healthcare USA, New York, NY, 2008, pp. 139-142.

Koide et al., "Hypertrophic response to hemodynamic overload: role of load vs. renin-angiotensin system activation". American Journal of Physiology—Heart, vol. 276, 1999, pp. H350-H358.

Kondo et al., "Characterization of conjugated metabolites of a new angiotensin II receptor antagonist, candesartan cilexetil, in rats by liquid chromatography/electrospray tandem mass spectrometry following chemical derivatization." Abstract, Journal of Mass Spectrometry, vol. 31, No. 8, Aug. 1996, pp. 873-878 (p. A-11).

Kumari et al., "Effect of Pre- and Posttreatment of Losartan in Feline Model of Myocardial Ischemic-Reperfusion Injury". Methods and Findings in Experimental and Clinical Pharmacology, vol. 26, No. 1, 2004, pp. 39-45.

Lactitol JEFC 1996, published in FNP 52 Add 4 (1996).

Lazaro et al., "Forum Original Research Communication: Long-Term Blood Pressure Control Prevents Oxidative Renal Injury." Antioxidants & Redox Signaling, vol. 7, Nos. 9 & 10, 2005, pp. 1285-1293.

(56)　　　　　References Cited

OTHER PUBLICATIONS

Lefebvre et al., "Angiotensin-converting enzyme inhibitors in the therapy of renal diseases". Journal of Veterinary Pharmacology and Therapeutics, vol. 27, 2004, pp. 265-281.

Li et al., "Efficacy evaluation of Telmisartan in treatment of dilated cardiomyopathy with heart failure". Chinese Heart Journal, vol. 18, No. 4, 2006, pp. 427-429.

Lim et al., "Angiotensin II Blockade Reverses Myocardial Fibrosis in a Transgenic Mouse Model of Human Hypertrophic Cardiomyopathy". Circulation, vol. 103, Feb. 2001, pp. 789-791. [Accessed at http://circ.ahaqjournals.org/ on Sep. 3, 2014].

Malike et al., "Permethrin Spot on Intoxication of Cats: Literature review and survey of veterinary practioners in Australia". Journal of Feline Medicine and Surgery, vol. 12, 2010, pp. 5-14.

Maltilol, JEFCA 1996, published in FNP 52 Add 4 (1996).

Sent, U., et al. "Comparison of efficacy of long-term oral treatment with telmisartan and benazepril in cats with chronic 1 kidney disease." Journal of veterinary internal medicine 29.6 (2015): 1479-1487.

Written Opinion of the International Search Authority PCT/EP2024/05884 (WO2025125409A1) mailed on Jul. 2, 2025.

Barber P.J., "The Kidney," Editors: Chandler E.A., Gaskell C.J., Gaskell R.M., Feline Medicine and Therapeutics, 3rd Edition, Blackwell Publishing, 2004.

Chakrabarti S., et al., "Clinicopathological Variables Predicting Progression of Azotemia in Cats with Chronic Kidney Disease," Journal of Veterinary Internal Medicine, Mar. 23, 2012, vol. 26, No. 2, pp. 275-281, J.B. Lippincott—ISSN 0891-6640, XP055063311, Retrieved from URL: http://dx.doi.org/10.1111/j.1939-1676.2011.

Chen J., "Small Animal Diseases," Beijing Agricultural University Press, The First Edition, First Print, Apr. 1993, pp. 6-10 (8 Pages).

Cupisti A., et al., Biomedicine and Pharmacotherapy, 2003, vol. 57, No. 3-4, pp. 169-172.

Extended European Search Report for European Application No. 23204038.6, dated Feb. 7, 2024, 09 Pages.

Extended European Search Report for European Application No. EP11186070.6, dated Mar. 8, 2012, 14 Pages.

Extended European Search Report for European Application No. EP11186078.9, dated Apr. 4, 2012, 19 Pages.

Extended European Search Report for European Application No. EP11186080.5, dated Mar. 21, 2012, 15 Pages.

Karallied Viberti, Journal of Human Hypertension, 2006.

Merck: "Chronic Kidney Disease (Chronic Renal Failure)," accessed on Dec. 13, 2010, 07 Pages.

Partial European Search Report for European Application No. 06121905.1, dated Mar. 6, 2007, 15 Pages.

Polzin D.J., et al., "Chronic Kidney Disease," Textbook of Veterinary Internal Medicine, 6th Edition, W.B. Saunders Company, 2005.

Polzin, et al., "Textbook of Veterinary Internal Medicine," 2005, vol. 2, pp. 1756-1785.

Remuzzi, et al., Journal of Clinical Investigation, 2006, vol. 116, No. 2, pp. 288-296.

Rysava R., et al., "Effect Of Telmisartan On Blood Pressure Control And Kidney Function In Hypertensive, Proteinuric Patients With Chronic Kidney Disease," Blood Pressure Monitoring, 2005, vol. 10, No. 4, pp. 207-213.

Sharma A.M., et al., "Telmisartan in Patients With Mild/Moderate Hypertension and Chronic Kidney Disease," Clinical Nephrology, 2005, vol. 63, No. 4, pp. 1-8.

The Merck Manual: "Chronic Kidney Diseases," 1 Page, [Retrieved On Aug. 4, 2010] Retrieved From URL: www. merck.com.

Wolf A.M., North American Veterinary Congress, 2006.

* cited by examiner

TELMISARTAN FOR THE TREATMENT OF HYPERTENSION IN DOGS

FIELD OF THE INVENTION

The present invention relates to telmisartan or a pharmaceutically acceptable salt thereof for use in a method for the treatment of hypertension in a dog in need of such treatment, wherein the method comprises administration of a therapeutically effective amount of telmisartan to the dog, wherein the therapeutically effective amount of telmisartan is administered in a daily dosage amount that is varied over a treatment period.

CROSS REFERENCE TO RELATED APPLICATIONS

This application is the national stage of International Application No. PCT/US2020/030581, filed Apr. 30, 2020, which claims the benefit of U.S. Provisional Application No. 62/871,749 filed Jul. 9, 2019, both of which are incorporated herein by reference.

BACKGROUND OF THE INVENTION

Systemic hypertension (SHT) is described as sustained systolic arterial blood pressure (SBP) over 140 mmHg, although interbreed differences in blood pressure have been described in dogs [1-4].

SHT recognition has increased in the last years improving the management of different diseases. SHT causes injury to tissues causing kidney damage resulting in proteinuria, retinopathy and hypertensive encephalopathy. These are called the target organ damage (TOD). The prevalence of hypertension is not perfectly established and varies from 1 to 10 percent in dogs [3].

Primary or idiopathic SHT is considered a rare condition in dogs due to the fact that only few cases have been diagnosed without an identifiable cause [4], but secondary SHT is relatively common and associated with different disorders as primary aldosteronism, hyperadrenocorticism, pheochromocytoma, chronic kidney disease (CKD) and hyperthyroidism as well as with some medications like glucocorticoids, mineralocorticoids, erythropoietin, non-steroidal anti-inflammatory drugs and inhibitors of tyrosine kinase [3, 5-9].

Idiopathic SHT is considered a health risk factor in itself. Severe consequences of SHT, described when SBP is over 180 mmHg, are retinopathy, intra-ocular hemorrhage and hypertensive encephalopathy, while the threshold for tissue injury is assumed to be 160 mmHg in cats and most breeds of dogs [4, 10]. Other conditions, including left ventricular hyper-trophy [11], proteinuria and further loss of functional kidney tissue [12], can be a cause or consequence of SHT. In addition, secondary SHT is considered an additional progression factor of the underlying disease.

The ACVIM Consensus Statement guidelines for the management of hypertension in dogs and cats propose different strategies including ACEI, calcium channel blockers (CCB), beta-blockers and diuretics. Monotherapy and daily dose administration is the first choice to control SHT, but some patients are refractory and need a combination of different drugs to achieve good control of SBP [3].

ACEIs are widely used as first-line treatment for SHT in dogs due to the role of the renin-angiotensin-aldosterone system (RAAS) in its development, but they provide an incomplete block of angiotensin II production that can result in poor control of SHT. This phenomenon, called 'aldosterone breakthrough', is due to the release of angiotensin II by other sites compared with those regulated by the ACE and independent of the dose of ACEI administered [14].

Amlodipine, a CCB, either by switching or as add-on therapy, is the alternative treatment when dogs are refractory to ACEI [6, 15]; however, aldosterone breakthrough may also occur in combined treatments with amlodipine and ACEI [16].

Although diuretics are frequently administered to hypertensive people, these agents are not first-choice drugs for veterinary patients, mainly in CKD where dehydration and volume depletion may prove problematic, but can be useful in hypertensive animals in which volume overload is apparent (e.g., those with edema) [3].

If an antihypertensive agent of choice is not completely effective, the usual approach is to increase the dosage or add an additional drug [13, 17]. However, certain combinations like ACEI and angiotensin II receptor blocker (ARB) must be used with caution or avoided, as recent publications in humans showed a higher risk of kidney failure in these cases [13, 18, 19].

Telmisartan, an ARB, is a novel drug used in veterinary medicine to reduce proteinuria associated with CKD in cats [20].

In dogs, it has been described that a daily oral dose of telmisartan produces vasodilation, diuresis and natriuresis without influencing potassium or creatinine excretion, and prevents potassium depletion by inhibiting the release of aldosterone in a dose-dependent manner [21, 22]. The standard recommended dose in the management of proteinuria in dogs is 1 mg/kg [13]. It has also been reported to have an effect on blood pressure in dogs at a 1 mg/kg daily dose [23].

In addition, a daily dose of 1.0 mg/kg of body weight of telmisartan has been used in combination with amlodipine in dogs to control systemic hypertension refractory to standard hypertension therapy [24].

In another case study, the successful management of refractory proteinuria and systemic hypertension in an 11-year old Yorkshire terrier with renal cell carcinoma with surgery, 0.43 mg/kg of telmisartan and 0.3 mg/kg of amlodipine has been described [25].

The International patent application WO 2019/008077 teaches an administration scheme of sartans for prophylaxis or treatment of hypertension in a cat, where the initial dosage is 1.0 to 5.0 mg/kg of bodyweight and is decreased in a subsequent period.

There is, therefore, a critical need for additional antihypertensive and sustainable options for canine patients suffering from systemic hypertension.

SUMMARY OF THE INVENTION

Now, it has been found that dogs can be treated against hypertension, in particular systemic hypertension (SHT) by administering therapeutically effective amounts of telmisartan, wherein the therapeutically effective amount of telmisartan is administered in a daily dosage amount that is varied over a treatment period, the daily dosage amount of telmisartan for a first period of time during the treatment period is at least 1.0 mg/kg of body weight, and the daily dosage amount of telmisartan is increased for a second period of time subsequent the first period of time during the treatment period.

Thus, one objective of the present invention consists in providing a new therapeutic approach for the treatment of dogs against systemic hypertension.

Therefore, the invention relates to telmisartan or a pharmaceutically acceptable salt thereof for use in a method for the treatment of hypertension, in a dog in need of such treatment, wherein the method comprises administration of a therapeutically effective amount of telmisartan to the dog, wherein the therapeutically effective amount of telmisartan is administered in a daily dosage amount that is varied over a treatment period, the daily dosage amount of telmisartan for a first period of time during the treatment period is at least 1.0 mg/kg of body weight, and the daily dosage amount of telmisartan is increased for a second period of time subsequent the first period of time during the treatment period.

Furthermore, the invention relates to telmisartan or a pharmaceutically acceptable salt thereof as a medicament for the treatment of hypertension in dogs, which are non-refractory to the treatment with ACE inhibitors.

In a further embodiment of the invention there is provided a method for the treatment of hypertension, in a dog in need of such treatment, wherein the method comprises administration of a therapeutically effective amount of telmisartan or a pharmaceutically acceptable salt thereof to the dog, wherein the therapeutically effective amount of telmisartan is administered in a daily dosage amount that is varied over a treatment period, the daily dosage amount of telmisartan for a first period of time during the treatment period is at least 1.0 mg/kg of body weight, and the daily dosage amount of telmisartan is increased for a second period of time subsequent the first period of time during the treatment period.

In a further embodiment, the invention provides a method for the treatment of hypertension in dogs, which are non-refractory to the treatment with ACE inhibitors, which method comprises administration of a therapeutically effective amount of telmisartan or a pharmaceutically acceptable salt thereof to a dog in need of such a treatment.

Furthermore the invention relates to a pharmaceutical composition for use in a method for the treatment of hypertension, in a dog in need of such treatment, which comprises telmisartan or a pharmaceutically acceptable salt thereof according to the invention and a pharmaceutically acceptable carrier.

DETAILED DESCRIPTION OF THE INVENTION

Figure 1:
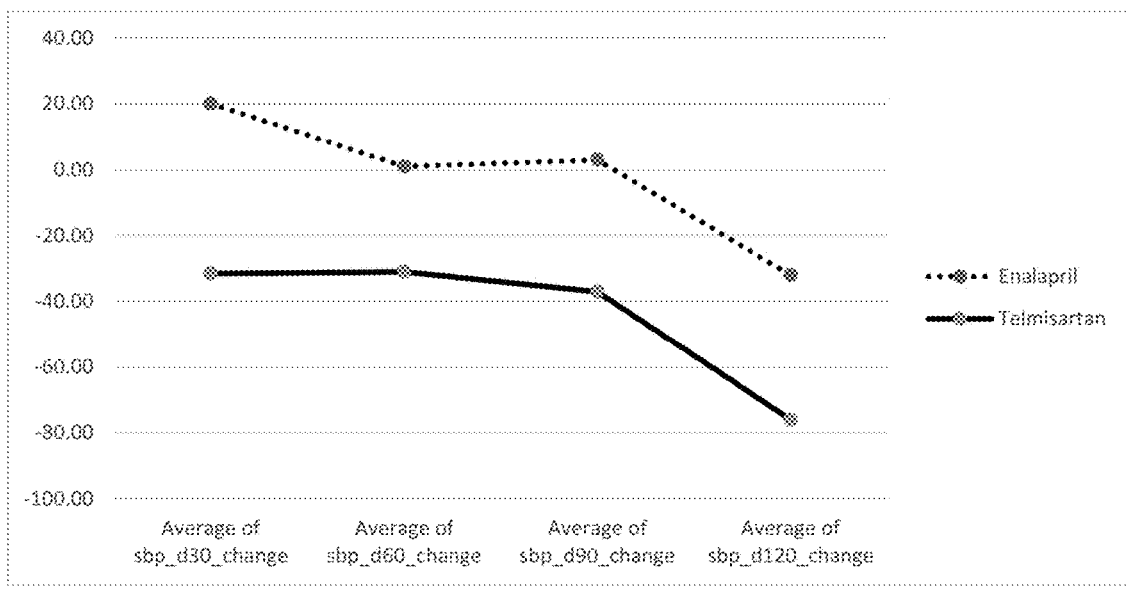
FIG. 1 is a plot of the average SBP change from baseline, from day 30 to day 120 in dogs with hypertension at day 0, which did not receive amlodipine; on day 90 the dogs received a dose of either enalapril or telmisartan in addition to the initial drug administered.

Before the embodiments of the present invention it shall be noted that as used herein and in the appended claims, the singular forms "a", "an", and "the" include plural reference unless the context clearly dictates otherwise. Thus, for example, reference to "a preparation" includes a plurality of such preparations, reference to the "carrier" is a reference to one or more carriers and equivalents thereof known to those skilled in the art, and so forth. Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was omitted from the description. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention.

Nothing herein is to be construed as an admission that the invention is not entitled to antedate such disclosure by virtue of prior invention.

The solution to the above technical problem is achieved by the description and the embodiments characterized in the claims.

In accordance with the present invention, methods are described herein for the treatment of hypertension in a dog in need of such treatment, where the methods comprise administration of a therapeutically effective amount of telmisartan to the dog, the therapeutically effective amount of telmisartan being administered in a daily dosage amount that is varied over a treatment period starting with an initial dose of at least 1.0 mg/kg of bodyweight. For example, the daily dosage amount of telmisartan for a first period of time during the treatment period can be 1.0 to 1.5 mg/kg of body weight, where the daily dosage amount of telmisartan is increased for a second period of time subsequent the first period of time during the treatment period.

As used herein, the term "pharmaceutically acceptable salts" includes the metal salts or the addition salts which can be used in dosage forms. For example, the pharmaceutically acceptable salts of the compounds provided herein can be acid addition salts, base addition salts or metal salts, and can be synthesized from parent compounds containing a basic or acid residue by means of conventional chemical processes. Such salts are generally prepared, for example, by reacting the free acid or base forms of these compounds with a stoichiometric amount of the suitable base or acid in water or in an organic solvent or in a mixture of both. Non-aqueous media are generally preferred, such as ether, ethyl acetate, ethanol, isopropanol, or acetonitrile. Examples of acid addition salts include mineral acid additions salts such as, for example, hydrochloride, hydrobromide, hydroiodide, sulfate, nitrate, phosphate, organic acid addition salts such as, for example, acetate, maleate, fumarate, citrate, oxalate, succinate, tartrate, malate, mandelate, methanesulfonate and p-toluenesulfonate. Examples of alkali addition salts include inorganic salts such as, for example, ammonium salts and organic alkaline salts such as, for example, diethylamine, ethylenediamine, ethanolamine, N,N-dialkylenethanolamine, triethanolamine, glutamine and basic amino acid salts. Examples of metal salts include, for example, sodium, potassium, calcium, magnesium, aluminium and lithium salts.

As used herein, the term "pharmaceutically acceptable" relates to molecular entities and compositions that are physiologically tolerable and do not normally cause an allergic reaction or a similar adverse reaction, such as gastric discomfort, dizziness and the like, when administered to humans. As used herein, the term "pharmaceutically acceptable" preferably means that it is approved by a regulatory agency of the federal or state government or listed in the US pharmacopoeia or another pharmacopoeia, generally recognized for its use in animals, preferably in mammals and more particularly in dogs.

As used herein, the term "hypertension" refers to refers to an elevated pressure of the blood against the walls of arteries during the time the heart contracts and empties itself of blood as well as during the time the heart relaxes and fills with blood and in. The term embraces systemic hypertension and idiopathic hypertension.

The term "systemic hypertension" is applied to sustained increases in systolic blood pressure (SBP>140 mmHg), and generally can be categorized into 1 of 3 types: (i) it may be caused by environmental or situational stressors, (ii) it may occur in association with other disease processes that increase BP (ie, secondary hypertension), or (iii) it may occur in the absence of other potentially causative disease processes (ie, idiopathic hypertension).

"Systemic hypertension" in dogs is classified based on the risk of target organ damage (TOD) according to the ACVIM consensus statement [26], as follows:

As used herein, the term "non-refractory to the treatment with ACE inhibitors" refers to dogs suffering from hypertension, which can be treated with an ACE inhibitor, but with less efficacy than telmisartan. To the contrary the high values of sustained systolic arterial blood pressure (SBP) of dogs that are refractory to ACE inhibitors cannot be lowered with the aid of ACE inhibitors.

In the non-refractory sub-population of dogs the efficacy of treatment with an ACE inhibitor is 10%, 15%, 20%, 25%, 30%, 35%, 40%, 45%, 50%, more than 50%, more than 60%, or more than 70% less effective than telmisartan for lowering their SBP values.

In a preferred embodiment the telmisartan and/or the method according to the invention relates to the treatment of the non-refractory subpopulation of dogs. However, the administration scheme according to the invention may advantageously be administered to both the subpopulations, the non-refractory as well as to refractory dogs.

The dogs to be treated with telmisartan according to the invention are preferably pet dogs of any breed including any kind of mongrel. Depending on the size of the breed or mongrel they may suffer from hypertension at an any age, but more frequently at an age of 5 years or more, preferably from 7 to 18 years, in particular from 10 to 16 years. Small breeds will as a rule suffer at a later age, preferably from 12 to 18, from this disease than big ones, which may be affected at an age of 10 to 16 years.

As used herein, the terms "together with" or "in combination with" covers both separate and sequential administration of telmisartan and another drug. For example, when the agents are administered sequentially, either the telmisartan or the other drug may be administered first. When administration is simultaneous, the agents may be administered either in the same or a different pharmaceutical composition. Adjunctive therapy, i.e. where one agent is used as a primary treatment and the other agent is used to assist that primary treatment, is also an embodiment of the present invention.

The one or more active ingredients may be used either as separate formulations or as a single combined formulation. When combined in the same formulation it will be appreciated that the two compounds must be stable and compatible with each other and the other components of the formulation.

Formulations of the invention include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation or insufflation administration. The most suitable route of administration may depend upon the condition and disorder of the patient. Preferably, the compositions of the invention are formulated for oral administration.

The formulations may conveniently be presented in unit dosage form and may be prepared by any of the methods well known in the art of pharmacy e.g. as described in "Remington: The Science and Practice of Pharmacy", Lippincott Williams and Wilkins, 21$^{st}$ Edition, (2005). Suitable methods include the step of bringing into association active ingredients with a carrier which constitutes one or more excipients. In general, formulations are prepared by uniformly and intimately bringing into association the active ingredients with liquid carriers or finely divided solid carriers or both and then, if necessary, shaping the product into the desired formulation. It will be appreciated that when the two active ingredients are administered independently, each may be administered by a different means.

Formulations suitable for oral administration may be presented as discrete units such as capsules, cachets or tablets, in particular chewable tablets, each containing a predetermined amount of active ingredient; as powder or granules; as a solution or suspension in an aqueous liquid or non-aqueous liquid; or as an oil-in-water liquid emulsion or water-in-oil liquid emulsion. The active ingredients may also be presented a bolus, electuary or paste.

Alternatively, the active ingredients may be incorporated into oral liquid preparations such as aqueous or oily suspensions, solutions, emulsions, syrups or elixirs. Formulations containing the active ingredients may also be presented as a dry product for constitution with water or another suitable vehicle before use. Such liquid preparations may contain conventional additives such as suspending agents (e.g. sorbitol syrup, methyl cellulose, glucose/sugar syrup, gelatin, hydroxymethyl cellulose, carboxymethyl cellulose, aluminium stearate gel and/or hydrogenated edible fats), emulsifying agents (e.g. lecithin, sorbitan mono-oleate and/or acacia), non-aqueous vehicles (e.g. edible oils, such as almond oil, fractionated coconut oil, oily esters, propylene glycol and/or ethyl alcohol), and preservatives (e.g. methyl or propyl p-hydroxybenzoates and/or sorbic acid).

In addition, the oral formulation may contain one or more flavoring agents, which enhance the compliance of the dog to be treated to chew and swallow the medication.

Most preferably telmisartan is administered orally in form of a chewable tablet or as an aqueous solution containing benzalkonium chloride as in the product Semintra®, which is commercially available from Boehringer Ingelheim Vetmedica GmbH, Ingelheim Germany.

In particular, the following items are disclosed herein:

a) Telmisartan or a pharmaceutically acceptable salt thereof for use in a method for the treatment of hypertension, in a dog in need of such treatment, wherein the method comprises administration of a therapeutically effective amount of telmisartan to the dog, wherein the therapeutically effective amount of telmisartan is administered in a daily dosage amount that is varied over a treatment period, the daily dosage amount of telmisartan for a first period of time during the treatment period is at least 1.0 mg/kg of body weight, and the daily dosage amount of telmisartan is increased for a second period of time subsequent the first period of time during the treatment period.

b) Telmisartan according to item a), wherein hypertension is associated with the elevated urinary protein-to creatinine concentration (UPC) levels.

c) Telmisartan according to item a) or b), which is the sodium or potassium salt thereof.

d) Telmisartan according to any of the items a) to c) for the treatment of dogs that are non-refractory to the treatment with ACE inhibitors.

e) Telmisartan according to any of the items a) to c) for the treatment of dogs that are refractory with ACE inhibitors.

f) Telmisartan according to any of the items a) to e), wherein the daily therapeutically effective amount thereof ranges from 1.0 to 10.0 mg/kg, preferably from 1.0 to 4.0 mg/kg, in particular from 1.0 to 3.5 mg/kg, most preferred from 1.0 to 3.0 mg/kg of body weight.

g) Telmisartan according to any of the items a) to f), wherein the daily dosage amount of telmisartan is increased for the second period of time by an incremental amount ranging from 0.25 to 2.50 mg/kg of body weight.

h) Telmisartan according to any of the items a) to g), wherein the daily dosage amount of telmisartan for a first period of time during the treatment period is 1.0 to 1.5 mg/kg of body weight, and the daily dosage amount of telmisartan for the second period of time is 1.75 to 3.50 mg/kg of body weight.

i) Telmisartan according to any of the items a) to h), wherein the daily dosage amount of telmisartan is decreased after the second period of time by an incremental amount ranging from 0.25 to 2.50 mg/kg of body weight.

j) Telmisartan according to any of the items a) to i), wherein the daily dosage amount of telmisartan is decreased after the second period of time upon a systolic blood pressure (SBP) value measured for the dog.

k) Telmisartan according to any of the items a) to j), wherein the daily dosage amount of telmisartan is decreased when a systolic blood pressure (SBP) value measured for the dog decreases after the second period of time by at least 10 mmHg or at least 20 mmHg or by 10 to 150 mmHg, 10 to 100 mmHg, 10 to 80 mmHg, 10 to 50 mmHg, 10 to 30 mmHg, 10 to 20 mmHg, 20 to 150 mmHg, 20 to 100 mmHg, 20 to 80 mmHg, 20 to 50 mmHg, or 20 to 30 mmHg in relation to a baseline SBP value measured for the dog prior to the first period of time.

l) Telmisartan according to any of the items a) to k), which is administered together with at least one other drug to a dog in need of such a treatment.

m) Telmisartan according to item l), wherein the other drug is selected from the group consisting of calcium channel blockers, preferably amlodipine, cardiotonic-calcium sensitizing agents, preferably pimobendan or levosimendan, ACE inhibitors, preferably ramipril, benazepril or enalapril, in particular enalapril.

n) Telmisartan according to any of the items a) to m), wherein the SBP of the dogs treated are lowered by at least at least 50%, or at least 40%, 30%, or 20% over a period of time. Preferably said period of time is period measured in days, such as 10 days, 20 days, 30 days, 60 days, 90 days, 120 days or more than 120 days up to a point in time when the SBP values are constantly well below the threshold of hypertension.

Figure 2:
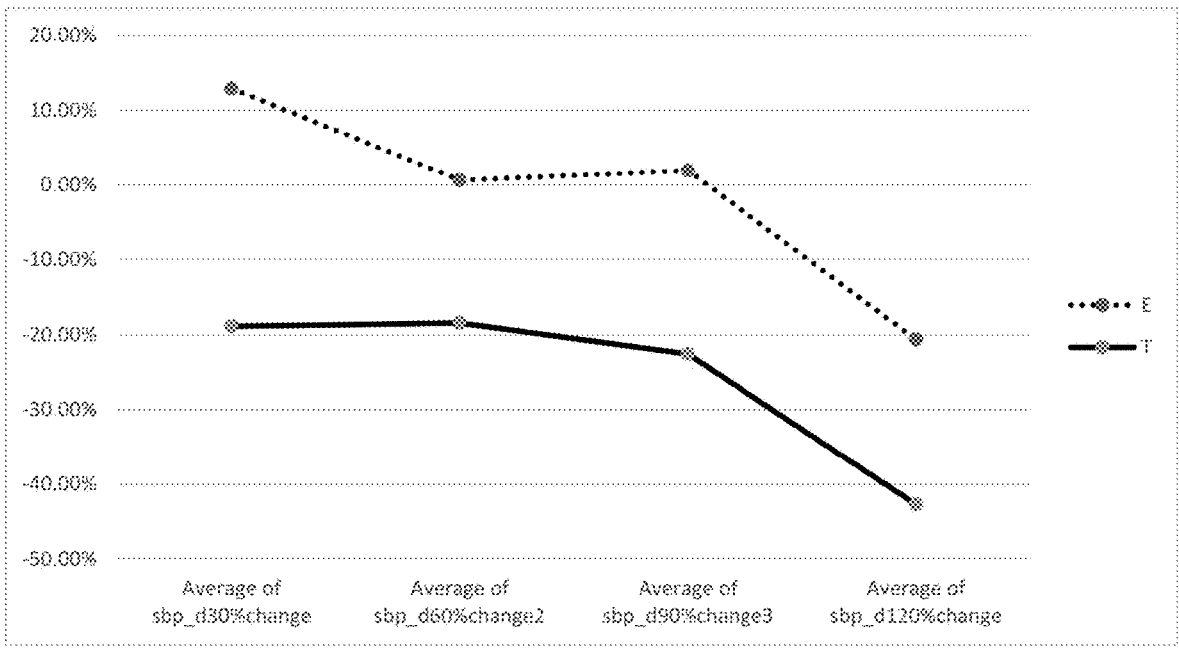
FIG. 2 is a plot of the average percent SBP change from baseline, from day 30 to day 120 in dogs with hypertension at day 0, which did not receive amlodipine; on day 90 the dogs received a dose of either enalapril (- - - ●- - - E) or telmisartan (-●- T) in addition to the initial drug administered.

A significantly greater proportion of telmisartan-treated dogs show a reduction of almost 20% in SBP at day 30, whereas the SBP in enalapril-treated dogs increased even by more than 10% as shown in FIG. 2.

As shown in FIG. 1 the average reduction in SBP is greater from day 30 to day 90 for telmisartan treated dogs compared to enalapril treated dogs. In addition, the combination of telmisartan and enalapril from day 90 to day 120 achieves a reduction of more than 40 mmHg of the average SBP in dogs which were treated with telmisartan from day 0 to day 90.

o) A method for the treatment of hypertension in a dog in need of such treatment, wherein the method comprises administration of a therapeutically effective amount of telmisartan or a pharmaceutically acceptable salt thereof to the dog, wherein the therapeutically effective amount of telmisartan is administered in a daily dosage amount that is varied over a treatment period, the daily dosage amount of telmisartan for a first period of time during the treatment period is at least 1.0 mg/kg of body weight, and the daily dosage amount of telmisartan is increased for a second period of time subsequent the first period of time during the treatment period.

p) The method according to item n), wherein hypertension is associated with elevated urinary protein-to creatinine concentration (UPC) levels.

q) The method according to item o) or p), which comprises administration of an effective amount of the sodium or potassium salt of telmisartan.

r) The method according to any of the items o) to q) for the treatment of dogs that are non-refractory or refractory to the treatment with ACE inhibitors.

s) The method according to one of the items o) to r), wherein the daily therapeutically effective amount of telmisartan ranges from 1.0 to 10.0 mg/kg, preferably from 1.0 to 4.0 mg/kg, in particular from 1.0 to 3.5 mg/kg, most preferred from 1.0 to 3.0 mg/kg of body weight.

t) The method according to one of the items o) to s), wherein the daily dosage amount of telmisartan is increased for the second period of time by an incremental amount ranging from 0.25 to 2.50 mg/kg of body weight.

u) The method according to one of the items o) to t), wherein the daily dosage amount of telmisartan is decreased after the second period of time by an incremental amount ranging from 0.25 to 2.50 mg/kg of body weight.

v) The method according to one of the items o) to u), wherein the daily dosage amount of telmisartan is decreased after the second period of time when the SBP value measured for the dog decreases by at least 20% in relation to a baseline SBP value measured for the dog prior to the first period of time.

w) The method according to one of the items o) to v), wherein the method further comprises administration of at least one other drug to such dog in need of such a treatment.

x) The method according to one of the items o) tow), wherein the other drug is selected from the group consisting of calcium channel blockers, cardiotonic-calcium sensitizing agents and ACE inhibitors.

y) The method according to one of the items o) to x),
wherein the other drug is selected from the group
consisting of amlodipine, pimobendan, levosimendan,
ramipril, benazepril and enalapril, in particular enal-
april.

z) The method according to one of the items o) to y),
wherein the SBP of the dogs treated are lowered by at
least at least 50%, or at least 40%, 30%, or 20% over
a period of time. Preferably said period of time is
period measured in days, such as 10 days, 20 days, 30
days, 60 days, 90 days, 120 days or more than 120 days
up to a point in time when the SBP values are con-
stantly well below the threshold of hypertension.

The invention now being generally described, will be
more readily understood by reference to the following
Examples, which are included merely for purposes of illus-
tration of certain aspects and embodiments of the present
invention, and are not intended to limit the invention.

EXAMPLES

Experimental Methods and Design.

A prospective, block-randomized, double-blind clinical
trial has been carried out. Fifty-four client-owned dogs with
persistent pathologic renal proteinuria have been recruited
over a 2-year period.

Example 1

Animals.

Azotemic and non-azotemic dogs (N=54) with hyperten-
sive and non-hypertensive CKD have been recruited pro-
spectively from patients presented to the hospital. Dogs
included as cases will have confirmed persistent pathologic
renal proteinuria due to CKD; in order to be classified as
such, fulfillment of the criteria described below will be
required.

Inclusion Criteria.

Included animals had an UPC level of approximately 2.0
(for non-azotemic patients; IRIS stage 1) or approximately
0.5 (for azotemic patients; IRIS stages 2-4), documented in
each of two urine samples collected 2 weeks apart. Abdomi-
nal ultrasound findings consistent with CKD (bilaterally
small, irregular kidneys) and absence of renal neoplasia have
also been documented.

Exclusion Criteria.

Animals have been excluded if one or more of the
following are identified: evidence of hemorrhage, inflam-
mation or bacteria on urine sediment analysis; positive urine
culture at the time of identification of proteinuria; positive
heartworm antigen test within 3 months of identification of
proteinuria and/or not currently receiving regular monthly
heartworm preventive; historical, physical examination or
clinical pathologic findings suggestive of acute kidney
injury, infectious nephropathy or lower urinary tract infec-
tion; systolic hypotension (SBP<120 mm Hg); moderate-to-
severe hyperkalemia (serum K>6.5 mmol/L); history of
having received oral ACEi and/or corticosteroids in the
month (ACEi) or 2 weeks (corticosteroids) preceding exami-
nation; concurrent illness associated with proteinuria, the
treatment of which might result in mitigation of proteinuria
(e.g, systemic lupus erythematosis, ehrlichiosis, neoplasia).
Dogs with suspected or confirmed hyper-adrenocorticism
and diabetes mellitus have been included if their disease is
considered well controlled with medical therapy.

Patient Grouping for Block Randomization:

Once included in the study and based on the presence/
degree of azotemia, dogs have been grouped according to
the International Renal Interest Society (IRIS) classification
scheme for CKD. Those classified as IRIS stages 2-4 (serum
creatinine ≥1.4 mg/dL with inappropriately dilute urine
[USG<1.030]) have been considered azotemic (AZ), and
those classified as IRIS stage 1 (creatinine <1.4 mg/dL) have
been considered non-azotemic (non-AZ). Within each of
these two groups, dogs will then be stratified according to
IRIS recommendations for arterial pressure (AP) substaging.
According to this scheme, dogs with persistent average
indirect arterial systolic BP<150 mm Hg will be classified as
AP0 (minimal risk for target organ damage). Those with
persistent average indirect arterial systolic BP≥150 mm Hg
have been classified as AP1-3 (at risk for target organ
damage). Four groups will thus be identified:

1. AZ (IRIS Stages 2-4), IRIS substage AP1-3 3. non-AZ
   (IRIS Stage 1), IRIS substage AP1-3
2. AZ (IRIS Stages 2-4), IRIS substage AP0 4. non-AZ
   (IRIS Stage 1), IRIS substage AP0

Once placed into one of these four groups, each patient
has then been assigned, based on a randomized blocking
scheme, to receive either enalapril (n=27) or telmisartan
(n=27), as described below, with the aim of grouping being
to ensure that equal numbers of each are included into the
two treatment groups.

Baseline.

On inclusion (day 0), all owners have been required to
read/sign a form consenting to their pets' participation in the
study. The following baseline data have been collected for
each case: full physical examination (performed by one of
the study investigators), fundic examination, blood pressure
measurement, serum chemistry panel, urinalysis, abdominal
ultrasound, UPC and urine culture. The results of screening
tests, if performed within 2 weeks of inclusion in the study,
may be used as baseline information. Baseline UPC has been
defined as the average of two measurements, taken 2 weeks
apart, prior to enrollment.

ARB/ACEI Therapy.

On day 0, each dog has been randomized to receive
telmisartan at 1 mg/kg PO q 24 h (TEL group, n=27) or
enalapril at 0.5 mg/kg PO q 12 h (ENAL group, n=27) in a
double-blind manner. Randomization and dispensation of
telmisartan or enalapril has been carried out at the appro-
priate doses. Owners have been provided with appropriate
contact numbers in the event of an emergency. Enalapril is
readily available and telmisartan has been provided by
Boehringer Ingelheim Vetmedica Inc., St. Joseph, MO in
form of the an aqueous solution, which is commercially
available as Semintra®.

Antihypertensive/Other Therapy.

For dogs that are classified as AP3 (SBP≥180 mmHg;
≥200 mmHg in sighthounds), a calcium channel blocker
(CCB; amlodipine, 0.1 mg/kg PO q 24 hours) has been
administered contemporaneously. Co-administration of
RAAS-inhibitors and CCB is common in human patients,
recommended by a panel of veterinary experts and shown to
be efficacious in a laboratory model of proteinuria. All dogs
have been started or maintained on a commercially available
diet formulated to be low in phosphorus and protein, for at
least 1 month prior to enrollment. During the study period,
diet remained constant. Treatment with fish oil has been
allowed, provided that the dog has been receiving this
supplement for >1 month at the time of enrollment.

Monitoring:

The monitoring protocol followed the recommendations
of the IRIS Canine GN Study Group Standard Therapy Subgroup. All dogs have been rechecked on day 7, at which time physical examination, SBP, serum creatinine (sCr) and serum potassium (K) have been evaluated. An increase in sCr of >30% compared to baseline or identification of moderate/severe hyperkalemia (serum K>6.5 mmol/L) or systolic hypotension (SBP<120) has prompt the investigator unmasking and removal of the patient from the study. For dogs in which average SBP of approximately 180 mm Hg was reliably identified (i.e. dogs classified as AP3), amlodipine will be up-titrated to 0.1 mg/kg PO BID. Thereafter, dogs classified as AP3 have been rechecked at 7-day intervals to ensure efficacy of therapy with adjustment of antihypertensive therapy. At each visit, if average SBP measurements remained at about 180 mm Hg, then the dog's amlodipine dose have been increased in increments of 0.05 mg/kg BID to a maximum dose of 0.3 mg/kg BID. SBP and sCr have been rechecked 7 d following any adjustments.

Final Phase I Visit.

On day 30, all dogs have undergone physical examination, SBP, serum biochemistry, urinalysis and UPC measurement. At this and all subsequent time points, urine for UPC measurement will consist of a pooled sample, created by combining three free-catch specimens collected and refrigerated by the owner on the preceding day.

Objective Endpoints.

The objective endpoints of phase I was the reduction of the SBP and the percentage change in UPC ($\Delta$UPC).

Conclusions.

The average change of SBP in telmisartan-treated dogs was -compared to enalapril-treated dogs—a reduction of at least 30 mmHg at day 30 as shown in FIG. 2.

Example 2

Specific Objectives #2 and #3 (Phases II and Ill; Intermediate-Term Phases)

Phase II of this study compared the efficacy of enalapril and telmisartan when these drugs were used as part of protocols that allow their up-titration, and phase III will evaluate their combination in dogs whose proteinuria persisted in the face of the highest doses of each drug alone. Each of the 54 dogs will remain in the treatment group to which he/she was assigned in phase I. Within these groups, up-titration of study drugs, followed by combination therapy have been performed if proteinuria persisted with UPC at about 0.5 on monthly rechecks.

ARB/ACEI Therapy.

Phase II (Days 31-90):

For those dogs in which UPC<0.5 was identified on day 30, treatment continued with telmisartan at a dose of 1 mg/kg PO q 24 h or enalapril at a dose of 0.5 mg/kg PO BID until the end of the study (day 120). For those in which UPC~0.5 was identified on day 30, the dose of study drug has been up-titrated monthly in increments of 1 mg/kg PO q 24 h (TEL group) or 0.5 mg/kg BID (ENAL group) until a target UPC<0.5 was attained OR a "ceiling dose" (3 mg/kg PO q 24 h for telmisartan or 1.5 mg/kg PO BID for enalapril) of either drug is reached, whichever occurs first.

Phase III (Days 91-120):

For those dogs in which UPC<0.5 was identified on or before day 90, treatment continued with telmisartan or enalapril at the dose producing proteinuria control until the end of the study. For those in which UPC approximately 0.5 was identified on day 90, enalapril at a dose of 0.5 mg/kg BID or telmisartan at a dose of 1 mg/kg q 24 h has been added for dogs in the TEL and ENAL groups, respectively. Combination therapy continued for 1 month, until the end of the study.

Monitoring.

If a change was made to an individual dog's treatment regimen on day 30, he/she has been rechecked one week later (day 37), at which time SBP, sCr and serum K levels have been evaluated. An increase in creatinine of >30% or identification of moderate/severe hyperkalemia (serum K>6.5 mmol/L) prompted the investigator unmasking and removal of the patient from the study. If mild hyperkalemia (serum K of 6.1-6.5 mmol/L) was identified, up-titration to the next dose has not been performed, regardless of UPC.

Thereafter, persistently proteinuric dogs have been monitored monthly (i.e., on days 60, 90) by means of SBP, UPC and urinalysis. Urine culture have been performed if active urinary sediment was identified. For dogs in which proteinuria persisted and up-titration of drug was required, SBP, sCr and serum K have been rechecked one week after adjustments (days 67, 97), with criteria for unmasking and further dose up-titration as outlined above. Dogs in which UPC<0.5 was identified at any time point have undergone recheck of monitoring parameters at the conclusion of the study only (d 120).

Final Visit:

On day 120, all dogs have undergone full physical examination, SBP, serum renal biochemistry, urinalysis (cystocentesis) and UPC measurement.

Objective Endpoints.

The objective endpoints for phase II included $\Delta$UPC from baseline and percentage of patients achieving 50% reduction or decrease to <0.5 of UPC following a total of 3 months of therapy, as well as an average reduction of SBP by about 20% from baseline. Phase III's objective endpoints included $\Delta$UPC from baseline, $\Delta$UPC over the month of therapy (UPCday90–UPCday120) and an average reduction of SBP by at least 40% from baseline.

Conclusions.

As shown in FIGS. 1 and 2 the average change in SBP was greater from day 30 to day 90 for telmisartan treated dogs compared to enalapril treated dogs with a greater change realized at day 90 for Telmisartan treated dogs.

In addition, the combination of Telmisartan and Enalapril from day 90 to day 120 lowers the average SBP by more than 70 mmHg and achieves in average a >40% reduction of the SBP in the group of dogs that were treated with telmisartan as shown in the following tables I and II.

TABLE I

| Average of SBP change | | | |
|---|---|---|---|
| Active Ingredient | SBP change [mmHg] day 30 | SBP change [mmHg] day 60 | SBP change [mmHg] day 90 | SBP change [mmHg] day 120 |
| Enalapril | +20.00 | +1.00 | +3.00 | −32.00[1] |
| Telmisartan | −31.50 | −31.00 | −37.00 | −76.00[2] |

[1]additional telmisartan has been administered after SBP measurement on day 90
[2]additional enalapril has been administered after SBP measurement on day 90

TABLE II

| | Average of SBP % change | | | |
| --- | --- | --- | --- | --- |
| Active Ingredient | SBP change [%] day 30 | SBP change [%] day 60 | SBP change [%] day 90 | SBP change [%] day 120 |
| Enalapril | +12.90 | +0.65 | +1.94 | −20.65[1] |
| Telmisartan | −18.88 | −18.42 | −22.58 | −42.70[2] |

[1]additional telmisartan has been administered after SBP measurement on day 90
[2]additional enalapril has been administered after SBP measurement on day 90

Figure 3:
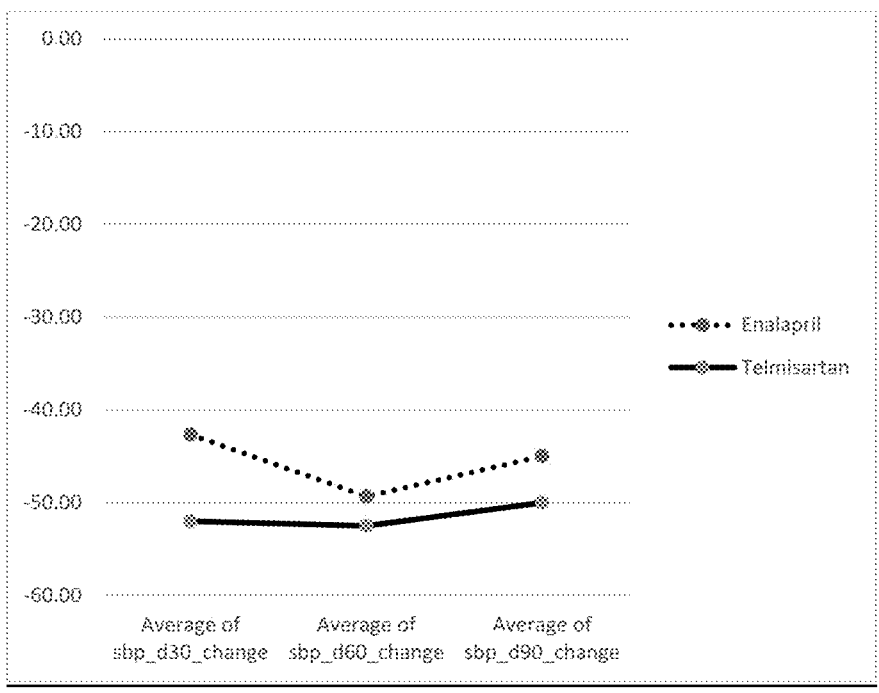
FIG. 3 depicts the average SBP change from baseline, from day 30 to day 90 in dogs with hypertension at day 0, which received amlodipine.

As shown in FIG. 3, the average SBP change from baseline was greater at day 30, day 60, and day 90 in dogs that were hypertensive with SBP of at least 150 mmHg at day 0, which received amlopdipine and the extra drug, in telmisartan treated dogs compared to those treated with enalapril.

Figure 4:
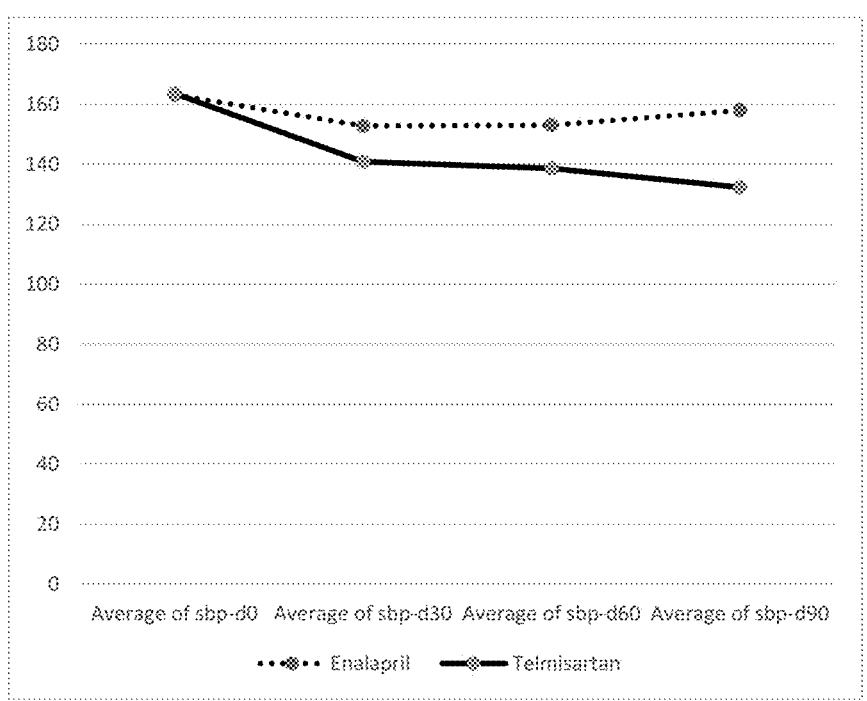
FIG. 4 depicts the average SBP in mmHg from day 0 to day 90 in dogs with hypertension at day 0, which did not receive amlodipine.

Moreover, the absolute average SBP of dogs that received telmisartan was much lower than of those dogs which were treated with enalapril as shown in FIG. 4. Whereas the SBP of the dogs treated with enalapril was reduced from 163 mmHg to 153 mmHg on day 30, but increased again on days 60 and 90, the average SBP values of the dogs treated with telmisartan was constantly lowered during the period of treatment from initially 163 mmHg to 132 mmHg on day 90 as shown in table III

TABLE III

| | Average of SBP | | | |
| --- | --- | --- | --- | --- |
| Active Ingredient | SBP [mmHg] day 0 | SBP [mmHg] day 30 | SBP [mmHg] day 60 | SBP [mmHg] day 90 |
| Enalapril | 163.17 | 153.80 | 153.00 | 158.00 |
| Telmisartan | 163.57 | 140.86 | 138.60 | 132.33 |

REFERENCES

The following publications are hereby incorporated by reference in their entirety as if each individual publication is specifically and individually indicated to be incorporated by reference. In case of conflict, the present application, including any definitions herein, will control.

[1] Bodey A R, Michell A R. Epidemiological study of blood pressure in domestic dogs. *J Small Anim Pract* 1996; 37:116-25.
[2] Brown S. Pathophysiology of systemic hypertension. In: Ettinger S J, Feldman E C, eds. *Textbook of veterinary internal medicine. Diseases of the dog and cat, vol. I.* 6th edn. St. Louis (Mo.): Elsevier Saunders, 2005:472-6.
[3] Brown S, Atkins C, Bagley R, et al. Guidelines for the identification, evaluation, and management of systemic hypertension in dogs and cats. *J Vet Intern Med* 2007; 21:542-58.
[4] Reusch C E, Schellenberg S, Wenger M. Endocrine hypertension in small animals. *Vet Clin North Am Small Anim Pract* 2010; 40:335-52.
[5] Cortadellas O, del Palacio M J, Bayón A, et al. Systemic hypertension in dogs with leishmaniasis: prevalence and clinical consequences. *J Vet Intern Med* 2006; 20:941-7.
[6] Geigy C A, Schweighauser A, Doherr M, et al. Occurrence of systemic hypertension in dogs with acute kidney injury and treatment with amlodipine besylate. *J Small Anim Pract* 2011; 52:340-6.
[7] Herring I P, Panciera D L, Werre S R. Longitudinal prevalence of hypertension, proteinuria, and retinopathy in dogs with spontaneous diabetes mellitus. *J Vet Intern Med* 2014; 28:488-95.
[8] Hanzlicek A S, Baumwart R D, Payton M E. Systolic arterial blood pressure estimated by mitral regurgitation velocity, high definition oscillometry, and Doppler ultrasonography dogs with naturally occurring degenerative mitral valve disease. *J Vet Cardiol* 2016; 18:22 6-33.
[9] Tjostheim S S, Stepien R L, Markovic L E, et al. Effects of Toceranib Phosphate on Systolic Blood Pressure and Proteinuria in Dogs. *J Vet Intern Med* 2016; 30:951-7.
[10] Leblanc N L, Stepien R L, Bentley E. Ocular lesions associated with systemic hypertension in dogs: 65 cases (2005-2007). *J Am Vet Med Assoc* 2011; 23 8:915-21.
[11] Takano H, Kokubu A, Sugimoto K, et al. Left ventricular structural and functional abnormalities in dogs with hyperadrenocorticism. *J Vet Cardiol* 2015; 17:173-81.
[12] Wehner A, Hartmann K, Hirschberger J. Associations between proteinuria, systemic hypertension and glomerular filtration rate in dogs with renal and non-renal diseases. *Vet Rec* 2008; 162:141-7.
[13] Brown S, Elliot J, Francey T, et al. IRIS Canine GN Study Group Standard Therapy Subgroup, Consensus Recommendations for Standard Therapy of Glomerular Disease in Dogs. *J Vet Intern Med* 2013; 27:S27-43.
[14] Ames M K, Atkins C E, Lee S, et al. Effects of high doses of enalapril and benazepril on the pharmacologically activated renin-angiotensin-aldosterone system in clinically normal dogs. *Am J Vet Res* 2015; 76:1041-50.
[15] Jepson R E, Elliott J, Brodbelt D, et al. Effect of control of systolic blood pressure on survival in cats with systemic hypertension. *J Vet Intern Med* 2007; 21:402-9.
[16] Ames M K, Atkins C E, Lantis A C, et al. Evaluation of subacute change in RAAS activity (as indicated by urinary aldosterone:creatinine, after pharmacologic provocation) and the response to ACE inhibition. *J Renin Angiotensin Aldosterone Syst* 2016; 17:1-12.
[17] Schmieder R E, Volpe M, Waeber B, et al. A guide for easy- and difficult-to-treat hypertension. *Int J Cardiol* 2014; 172:17-22.
[18] St Peter W L, Odum L E, Whaley-Connell A T. To RAS or not to RAS? The evidence for and cautions with renin-angiotensin system inhibition in patients with diabetic kidney disease. *Pharmacotherapy* 2013; 33:496-514.
[19] European Medicines Agency. *PRAC recommends against combined use of medicines affecting the renin-angiotensin (RAS) system,* 2014. EMA EMA/196502/2014.
[20] Sent U, Gössl R, Elliott J, et al. Comparison of Efficacy of Long-term Oral Treatment with Telmisartan and Benazepril in Cats with Chronic Kidney Disease. *J Vet Intern Med* 2015; 29:1479-87.
[21] Wienen W, Entzeroth M, Meel J C A, et al. A Review on Telmisartan: A Novel, Long-Acting Angiotensin II-Receptor Antagonist. *Cardiovasc Drug Rev* 2000; 18: 127-54.
[22] Schierok H, Pairet M, Hauel N, et al. Effects of telmisartan on renal excretory function in conscious dogs. *J Int Med Res* 2001; 29:131-9.
[23] Coleman A E, Schmiedt C W, Handsford C G, et al. Attenuation Of The Pressor Response To Exogenous Angiotensin By Angiotensin Receptor Blockers In Normal Dogs. *J Vet Intern Med* 2014; 28.

[24] Caro-Vadillo A, Daza-González M A, Gonzalez-Alonso-Alegre E, et al. *Effect of a combination of telmisartan and amlodipine in hypertensive dogs*. Vet Rec Case Rep 2018; 6:e000471.

[25] Kwon Y-J, Suh G-H, Kang S-S, Kim H-J, *Can Vet J* 2018; 59:759-762.

[26] Guidelines for the identification, evaluation, and management of systemic hypertension in dogs and cats, Mark J. Acierno et al, *J Vet Intern Med,* 2018

What is claimed is:

1. A method for the treatment of hypertension in a dog in need of such treatment, wherein the dog has a systolic blood pressure (SBP) greater than 140 mmHg and the method comprises administration of a therapeutically effective amount of telmisartan or a pharmaceutically acceptable salt thereof to the dog, wherein the therapeutically effective amount of telmisartan is administered in a daily dosage amount that is varied over a treatment period, the daily dosage amount of telmisartan for a first period of time during the treatment period is at least 1.0 mg/kg of body weight, and the daily dosage amount of telmisartan is increased for a second period of time subsequent the first period of time during the treatment period and in which an identified urinary protein-to-creatinine concentration (UPC) ratio is at least 0.5.

2. The method according to claim 1, wherein the hypertension is associated with systemic chronic kidney disease (CKD), elevated urinary protein-to-creatinine ratio (UPC) levels and/or hyperthyroidism.

3. The method according to claim 1, which comprises administration of an effective amount of the sodium or potassium salt of telmisartan.

4. Telmisartan according to claim 1, wherein the hypertension is idiopathic hypertension.

5. The method according to claim 1, wherein the daily therapeutically effective amount of telmisartan ranges from 1.0 to 10.0 mg/kg of body weight.

6. The method according to claim 1, wherein the daily dosage amount of telmisartan is increased for the second period of time by an incremental amount ranging from 0.25 to 2.50 mg/kg of body weight.

7. The method according to claim 6, wherein the daily dosage amount of telmisartan for a first period of time during the treatment period is 1.0 to 1.5 mg/kg of body weight, and the daily dosage amount of telmisartan for the second period of time is 1.75 to 4.0 mg/kg of body weight.

8. The method according to claim 1, wherein the daily dosage amount of telmisartan is decreased after the second period of time by an incremental amount ranging from 0.25 to 2.50 mg/kg of body weight.

9. The method according to claim 1, wherein the daily dosage amount of telmisartan is decreased after the second period of time based upon measuring the systolic blood pressure (SBP) value measured for the dog.

10. The method according to claim 9, wherein daily dosage amount of telmisartan is decreased when the systolic blood pressure (SBP) value measured for the dog decreases after the second period of time by at least 10 mmHg or at least 20 mmHg or by 10 to 150 mmHg, 10 to 100 mmHg, 10 to 80 mmHg, 10 to 50 mmHg, 10 to 30 mmHg, 10 to 20 mmHg, 20 to 150 mmHg, 20 to 100 mmHg, 20 to 80 mmHg, 20 to 50 mmHg, or 20 to 30 mmHg in relation to a baseline SBP value measured for the dog prior to the first period of time.

11. The method according to claim 1, wherein the method further comprises administration of at least one other drug to such dog in need of such a treatment.

12. The method according to claim 11, wherein the other drug is selected from the group consisting of calcium channel blockers, cardiotonic-calcium sensitizing agents and ACE inhibitors.

13. The method according to claim 12, wherein the other drug is selected from the group consisting of amlodipine, pimobendan, levosimendan, ramipril, benazepril and enalapril.

14. The method according to claim 1, wherein the hypertension of the dog in need of such treatment is non-refractory to the treatment with ACE inhibitors.

15. A method for the treatment of hypertension in a dog in need of such treatment, wherein the dog has a systolic blood pressure (SBP) greater than 140 mmHg and the method comprises administration of a therapeutically effective amount of telmisartan or a pharmaceutically acceptable salt thereof to the dog, wherein the therapeutically effective amount of telmisartan is administered in a daily dosage amount that is varied over a treatment period, a first daily dosage amount of telmisartan is administered for a first period of time during the treatment period, and a second daily dosage amount of telmisartan is administered for a second period of time subsequent the first period of time during the treatment period and based upon a change in an identified urinary protein-to-creatinine concentration (UPC) ratio determined for the dog.

\* \* \* \* \*